US012765776B2

(12) United States Patent
Park

(10) Patent No.: US 12,765,776 B2
(45) Date of Patent: Oct. 20, 2026

(54) SCALP SENSING DEVICE AND SCALP ANALYSIS SYSTEM INCLUDING THE SAME

(71) Applicant: Becon Co., Ltd, Gyeonggi-do (KR)

(72) Inventor: Min Suk Park, Gyeonggi-do (KR)

(73) Assignee: Becon Co., Ltd., Gyeonggi-do (KR)

( * ) Notice: Subject to any disclaimer, the term of this patent is extended or adjusted under 35 U.S.C. 154(b) by 388 days.

(21) Appl. No.: 18/521,858

(22) Filed: Nov. 28, 2023

(65) Prior Publication Data

US 2024/0215828 A1 Jul. 4, 2024

(30) Foreign Application Priority Data

Dec. 30, 2022 (KR) ........................ 10-2022-0190290

(51) Int. Cl.
*A61B 5/00* (2006.01)

(52) U.S. Cl.
CPC .......... *A61B 5/0077* (2013.01); *A61B 5/0071* (2013.01); *A61B 5/0082* (2013.01); *A61B 5/448* (2013.01)

(58) Field of Classification Search
CPC ... A61B 5/0077; A61B 5/0071; A61B 5/0082; A61B 5/448; A61B 5/0075; A61B 5/1032; A61B 5/441; A61B 5/443; A61B 5/00; A61B 5/446; A61B 5/0059; A61B 5/0064; A61B 5/01; A61B 5/7275; A61B 5/7282; A61B 1/043; A61B 1/0607; A61B 1/0615; A61B 1/0623; A61B 1/0625; A61B 1/0627; A61B 1/0638; A61B 1/0646; A61B 5/445; A61B 5/442; A61B 5/444; A61B 1/00186; A61B 5/4266; A61B 5/4272; A61B 2018/00166; A61B 2562/166; G01J 3/10; G01J 2003/003; G01J 3/0202; G01J 3/0256; G01J 3/0262; G01J 3/0272; G01J 3/0289; G01J 3/0291; G01J 3/08; G01J 2003/106; G01J 2003/102; G01J 1/0488; G01J 1/0403; G01J 1/0422; G01J 1/0233; G01J 1/0204; H04N 23/11; H04N 23/125
USPC .......................................................... 600/310
See application file for complete search history.

(56) References Cited

U.S. PATENT DOCUMENTS

2015/0230863 A1* 8/2015 Youngquist .......... A61B 18/203 606/9

FOREIGN PATENT DOCUMENTS

| | | | | |
|---|---|---|---|---|
| GB | 2444855 A * | 6/2008 | ......... | G01N 21/6486 |
| JP | 2022-62221 | 4/2022 | | |
| JP | 2022-141203 | 9/2022 | | |
| KR | 20170037737 A * | 4/2017 | ........... | A61B 5/0064 |

(Continued)

*Primary Examiner* — Brian L Casler
(74) *Attorney, Agent, or Firm* — WOMBLE BOND DICKINSON (US) LLP

(57) ABSTRACT

Provided is a portable scalp sensing device including a camera module, wherein the camera module includes a camera part including an image sensor and a lens, a light diffusion member disposed on an optical axis of the camera part, a blue-cut filter disposed between the camera part and the light diffusion member to block light of a predetermined wavelength that is incident on the camera part, a UV light source, and a white light source, the light diffusion member may guide light diffused from each of the white light source and the UV light source to illuminate a measurement target region with the light, and the camera part may obtain an image of the measurement target region illuminated by the light.

13 Claims, 16 Drawing Sheets

(56) References Cited

FOREIGN PATENT DOCUMENTS

| | | | | |
|---|---|---|---|---|
| KR | 10-2018-0010672 | | 1/2018 | |
| KR | 10-2019-0120037 | | 10/2019 | |
| KR | 10-2118099 | | 6/2020 | |
| KR | 10-2021-0041266 | | 4/2021 | |
| KR | 10-2260260 | | 6/2021 | |
| KR | 10-2022-0138631 | | 10/2022 | |
| WO | WO-2017155265 | A1 * | 9/2017 | ................ F21V 9/00 |

* cited by examiner

SCALP SENSING DEVICE AND SCALP ANALYSIS SYSTEM INCLUDING THE SAME

CROSS-REFERENCE TO RELATED APPLICATION

This application claims priority to and the benefit of Korean Patent Application No. 2022-0190290, filed on Dec. 30, 2022, the disclosure of which is incorporated herein by reference in its entirety.

BACKGROUND

1. Field of the Invention

The present invention relates to a scalp sensing device and a scalp analysis system including the same, and more particularly, to a small-sized, portable scalp sensing device that can simultaneously obtain a scalp image, an ultraviolet (UV)-induced fluorescence image, and scalp environment data and a scalp analysis system including the scalp sensing device.

2. Discussion of Related Art

"Alopecia" means loss of hair from where hair would normally be present and typically refers to loss of terminal hair on the scalp. Due to the negative impact of alopecia, alopecia has been recognized as a serious social problem. In recent years, the age group of people experiencing alopecia has gradually become younger, to people in their twenties or thirties. Also, the number of women with female pattern baldness has also sharply increased. Accordingly, the alopecia-related market is steadily growing.

Alopecia occurs over a long period of time. After a hair thinning process in which hair gets thinner and weaker, the anagen phase is shortened and hair in the telogen phase that prepares to shed increases. Then, due to follicular failure, a follicular dystrophy state in which a problem occurs in the supply of nutrients to hair occurs, which leads to a later stage of alopecia in which hair that has not grown to terminal hair falls out.

Therefore, early diagnosis and continuous monitoring are important, but in a conventional method of determining a scalp condition, a scalp condition of an individual is observed by visual inspection after the individual directly visits a hospital or clinic. In this case, there is an inconvenience that the individual has to directly visit a hospital or clinic to receive a consultation or diagnosis, and there is a limitation in that it is difficult to obtain objective measurement and determination results for the current state of alopecia.

Therefore, in addition to visual inspection by a specialist, accurate diagnosis based on objective measurement data through sensing data including a scalp image is necessary, and there is a need for development of a device and system allowing a user to identify and diagnose a scalp condition easily and conveniently at will.

For analysis of a scalp or skin condition, a method using both a typical scalp image and an ultraviolet (UV)-induced fluorescence image is known. UV-induced fluorescence is a phenomenon in which, when a target site of the skin or scalp is irradiated with UV light, a change in an energy level occurs in vivo in terms of sebum, dead follicles, inflammation, or the like, and visible light is emitted. Using such a phenomenon, porphyrin or sebum information can be visually obtained. However, in a spectrum of visible light emitted due to sebum, dead follicles, inflammation, or the like, blue light having a wavelength in a range of 360 nm to 440 nm enters a camera in large amounts, and there is a problem in that the camera is not able to capture information on things such as sebum, dead follicles, inflammation, or the like that is desired to be captured.

A conventional skin or scalp measurement device illuminates the skin with UV light in a state in which external light is blocked and uses a blue-cut filter so that information on things such as sebum (white-orange), dead follicles (purple-black), inflammation (orange-red), or the like is expressed well in an image.

However, in the case of the conventional method, there is a problem of an increase in the size of a device due to requiring a blackout curtain for UV fluorescence excitation imaging. Also, when skin is observed by interchangeably using a camera with a white light source and a camera with a UV light source, it is not easy to observe the skin at the same position.

When a polarizing filter and a UV blocking filter are used together to obtain both images using a single camera in order to address the above problems, a light quantity is insufficient, and it is difficult to maximize a light emission effect by UV light.

Also, conventional devices that only capture scalp images have limitations in collection of data for analyzing scalp health, such as moisture, temperature, and smell of the scalp. Each sensor should be provided as a separate device, or in order to measure various factors of the scalp using multiple sensors, a mode should be manually changed to Camera, Sensor 1, Sensor 2, and the like, and moisture, temperature, oil, or the like should be sequentially measured one at a time, and thus there are problems in that it is difficult to secure consistency of measurement data of the same site, and it is difficult and cumbersome for a non-specialist user to operate the device.

(Patent Document 1) KR 2019-0120037 A

SUMMARY OF THE INVENTION

The present invention is directed to a small-sized, portable scalp sensing device that can obtain various scalp measurement data in one measurement.

The present invention is also directed to a scalp sensing device and a scalp analysis system that can simultaneously obtain a scalp image and an ultraviolet (UV)-induced fluorescence image, which are easy to match by white light, for the same site on the scalp.

According to an aspect of the present invention, there is provided a portable scalp sensing device including a camera module. The camera module includes a camera part including an image sensor and a lens, a light diffusion member disposed on an optical axis of the camera part, a blue-cut filter disposed between the camera part and the light diffusion member to block light of a predetermined wavelength that is incident on the camera part, a UV light source, and a white light source.

The light diffusion member may diffuse and guide light emitted from each of the white light source and the UV light source to direct the light onto a measurement target region. The camera part may capture images of the measurement target region illuminated by the emitted light. The white light source and the UV light source alternately emit light and the white light and the UV light may alternately illuminate the measurement target region through the light diffusion member.

The predetermined wavelength may be in a range of 360 nm to 440 nm, and the UV light source may be a UV-light emitting diode (LED) that is disposed under the light diffusion member. The white light source may be an LED that is disposed adjacent to an outer side of the light diffusion member. The white light source and the UV light source may be controlled to sequentially emit light, and the camera part may be controlled to sequentially obtain an image of the measurement target region from irradiation of white light and a porphyrin excitation image of the measurement target region from irradiation of UV light.

The scalp sensing device may further include a support plate having a through-hole formed therein, the blue-cut filter may be disposed at an upper end of the through-hole and block the through-hole, and the camera part may be disposed at a bottom portion of the through-hole. The camera part may detect light incident through the blue-cut filter and the through-hole, and a plurality of white light sources may be fixed to the support plate and disposed to be symmetrical about the optical axis at the outer side of the light diffusion member.

The light diffusion member may be formed as one body made of a transparent plastic material and may have a double cylinder structure in which an inner cylinder having a hollow portion formed therein and an outer cylinder, which has an upper end connected to the inner cylinder and extends downward, are coupled along a central axis of the hollow portion. The UV light source may be disposed between the inner cylinder and the outer cylinder.

The central axis of the hollow portion may be coaxial with the optical axis. The inner cylinder and the outer cylinder may be coaxial, may be connected at an upper portion to share the same inner and outer circumferential surfaces, and may be spaced apart from each other at a lower portion so that a lower space is formed between the inner and outer cylinders.

With the above-described structure, it is possible to implement a small-sized scalp sensing device that can simultaneously obtain a scalp image and a UV-induced fluorescence image of excellent quality with a single camera part.

An intermediate portion may be formed at a circumference of the inner cylinder and disposed between the inner cylinder and the outer cylinder. The intermediate portion may be branched downward from an outer circumferential portion of the inner cylinder and extend vertically, and an inner circumferential surface of a lower end of the intermediate portion may be configured in a shape corresponding to the blue-cut filter to circumscribe a side edge of the blue-cut filter.

One or more connecting portions may be formed to radially extend from the inner cylinder of the light diffusion member about the optical axis and be connected to the outer cylinder. The white light sources may be disposed adjacent to outer sides of the one or more connecting portions so that each white light source faces one of the connecting portions.

The scalp sensing device may further include a scalp environment sensor, and an upper casing configured to cover the camera module and the scalp environment sensor.

The scalp environment sensor may include one or more of a temperature sensor, a moisture sensor, and a volatile organic compound (VOC) sensor fixed to the support plate. The camera module may be disposed adjacent to the scalp environment sensor.

The upper casing may include a camera part cap configured to tightly cover an upper portion of the light diffusion member disposed at an upper end of the camera module and an environment sensor cap configured to cover the scalp environment sensor. A plurality of through-portions may be formed in the environment sensor cap.

The camera part cap may have a protruding cylindrical shape and may be able to come in close contact with the scalp while a scalp image is being captured.

The scalp sensing device may have a separate cradle for mounting the scalp sensing device, and the cradle may include an electrical contact part for charging and a UV sterilizer.

The scalp sensing device may further include a separation plate disposed under the light diffusion member. The separation plate may be made of a non-light-transmissible material and may have a through-portion formed at a center and a blocking wall formed to protrude upward from a circumference of the through-portion. The blue-cut filter may be seated on a seating portion formed at the blocking wall and may be positioned at an upper end of the through-portion. A central axis of the through-portion at the center may be coaxial with the optical axis, and the UV light source may be disposed at an outer side of the blocking wall. The white light source may be positioned more outward from the optical axis than the UV light source, and the light diffusion member may be disposed on the separation plate.

According to another aspect of the present invention, there is provided a sensing device for sensing skin or scalp, the sensing device including: a main body part including a battery, a main printed circuit board (PCB), and a main body frame to which the battery and the main PCB are fixed; and a sensor module coupled to the main body part and including a camera module mounted on a sensor board.

The camera module may include a camera part including an image sensor and a lens and positioned under a through-hole of the sensor board, a light diffusion member disposed on an optical axis of the camera part, a blue-cut filter disposed between the camera part and the light diffusion member to block the through-hole and block light of a predetermined wavelength that is incident on the camera part, a UV light source, and a white light source.

The light diffusion member may diffuse and guide light emitted from each of the white light source and the UV light source to illuminate a measurement target region with the light. The camera part may obtain images of the measurement target region illuminated by the light, and the camera part may detect light passing through the through-hole through the blue-cut filter.

The light diffusion member may be formed as one body made of a light-transmissible material and may have a double cylinder structure in which an inner cylinder having a hollow portion formed therein and an outer cylinder, which has an upper end connected to the inner cylinder and extends downward, are coupled along a central axis of the hollow portion. The UV light source may be disposed between the inner cylinder and the outer cylinder.

The main PCB may include a memory, a processor, and a communication module. The sensor module may include an environment sensor disposed adjacent to the camera module on the sensor board.

The environment sensor may include one or more of a temperature sensor, a moisture sensor, and a volatile organic compound (VOC) sensor fixed onto the sensor board.

The sensor module may be covered by an upper casing, and the upper casing may include a camera part cap formed to protrude to tightly cover an upper portion of the light diffusion member, and the camera part cap may be able to come in close contact with the scalp or skin while an image thereof is being captured.

According to still another aspect of the present invention, there is provided a scalp analysis system including the scalp sensing device, an electronic device, and a server. The scalp sensing device obtains scalp sensing data of an animal and sends the scalp sensing data to the electronic device or the server through a communication network. The scalp sensing data may be scalp image data, scalp temperature data, scalp moisture data, or scalp smell data.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
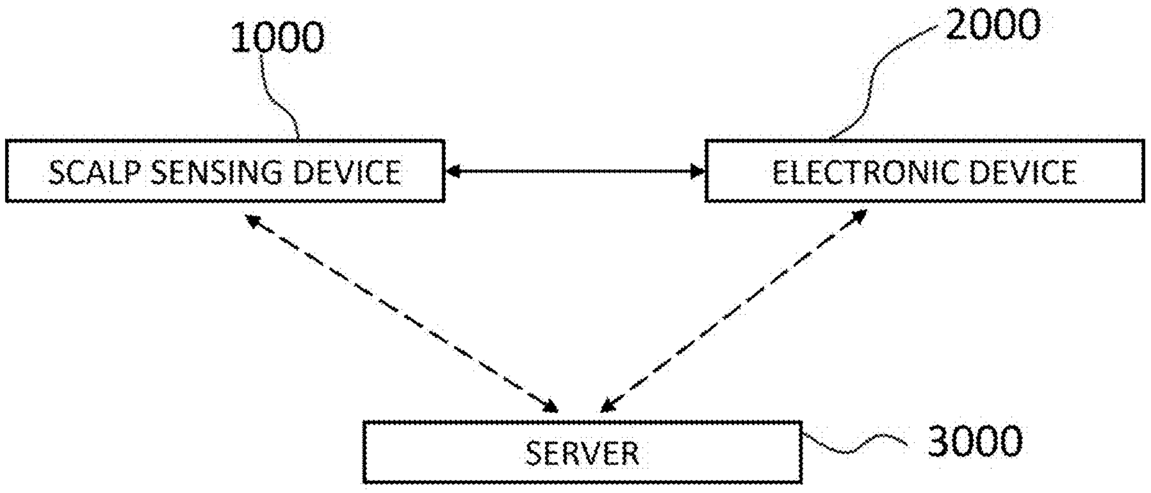
FIG. 1 is a schematic diagram of a scalp analysis system according to one embodiment of the present invention.

Hereinafter, embodiments of the present invention will be described in detail with reference to the accompanying drawings so that those of ordinary skill in the art to which the present invention pertains can easily carry out the present invention. However, the present invention may be implemented in various different forms and is not limited to the embodiments described herein. Also, in the drawings, in order to clearly describe the present invention, parts irrelevant to the description are omitted, and in principle, the same reference numerals represent the same components throughout the specification. Also, components having the same function within the scope of the same spirit shown in the drawings of each embodiment are described using the same reference numerals, and repeated description thereof is omitted. In this process, thicknesses of lines or sizes of components illustrated in the drawings may be exaggerated for clarity and convenience of description.

When detailed description of a known function or configuration relating to the present application is deemed as having the possibility of unnecessarily obscuring the gist of the present application, the detailed description thereof will be omitted. Also, ordinals (for example, first, second, etc.) used in the process of describing the present specification are only identification numbers for distinguishing one component from another component.

Also, the terms "module" and "part" used in the names of the components according to the following embodiments have been imparted or used together only in consideration of ease of writing the specification, and such terms do not have distinct meanings or play distinct roles by themselves.

Throughout the specification, when a certain part is described as being "connected" or "coupled to another part, this not only includes a case in which the part is "directly connected" or "directly coupled" to the other part, but also includes a case in which the part and the other part are "connected" or "coupled" to each other with another part disposed therebetween. Also, when a certain part is described as "including" a certain component, unless particularly described otherwise, this means that the part may further include other components instead of excluding other components.

Hereinafter, exemplary embodiments of the present invention will be described in detail with reference to the accompanying drawings.

FIG. 1 is a schematic diagram of a scalp analysis system according to one embodiment of the present application. Referring to FIG. 1, the scalp analysis system according to one embodiment of the present application may include a scalp sensing device 1000, an electronic device 2000, and a server 3000.

The scalp sensing device 1000 may obtain scalp image data, scalp temperature data, scalp moisture data, or scalp smell data. The scalp sensing device 1000 may transmit the obtained scalp image and/or scalp temperature data, scalp moisture data, or scalp smell data (hereinafter referred to as "scalp sensing data") to the electronic device 2000 or the server 3000 through an arbitrary network.

Hereinafter, a configuration of the scalp sensing device 1000 according to one embodiment of the present invention will be described in detail with reference to FIGS. 2 to 14.

Figure 2:
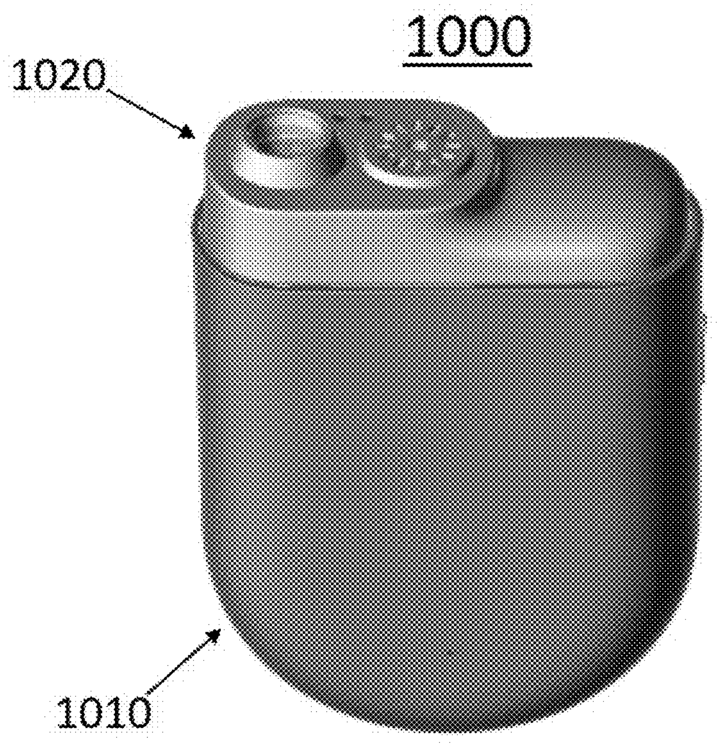
FIG. 2 is a perspective view of a scalp sensing device (1000) according to one embodiment of the present invention.

FIG. 2 is a perspective view of the scalp sensing device 1000 according to one embodiment of the present invention.

Figure 3:
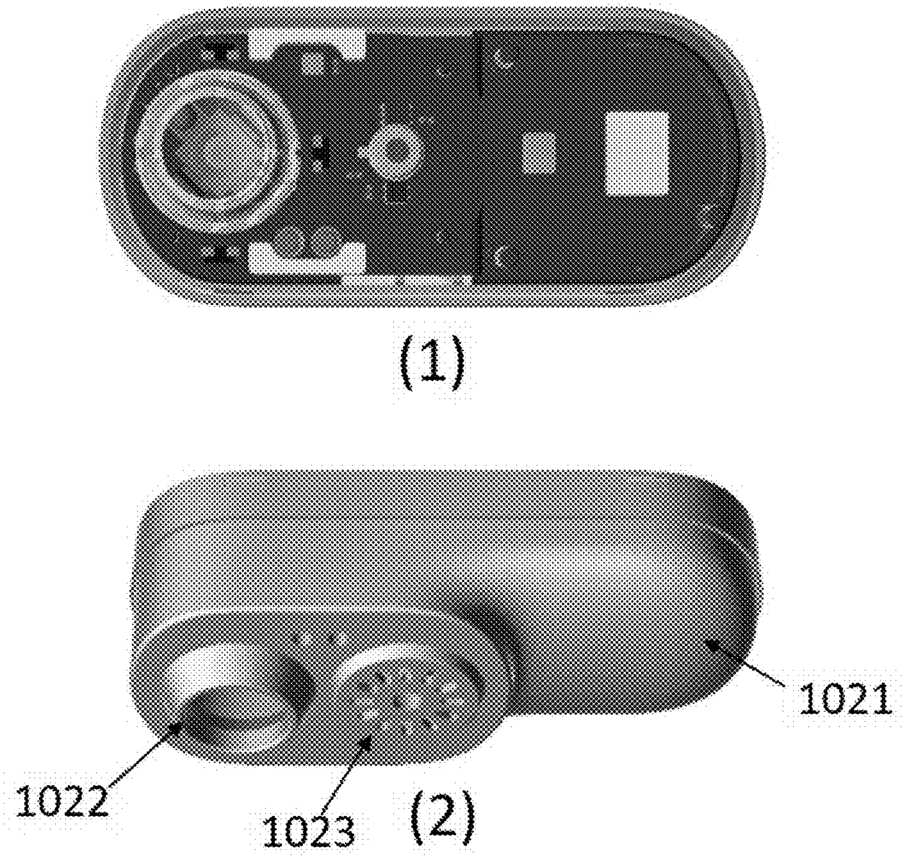
FIG. 3 is (1) a top view of a state in which an upper casing (1021) is disassembled from the scalp sensing device (1000) according to one embodiment of the present invention and (2) a perspective view of the upper casing (1021)
Figure 4:
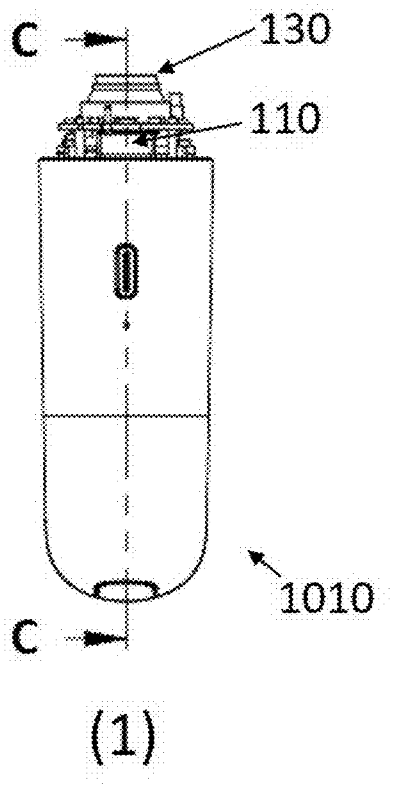
FIG. 4 shows a lateral view and a longitudinal cross-sectional view of the scalp sensing device (1000) in a state in which the upper casing is removed according to one embodiment of the present invention.
Figure 4:
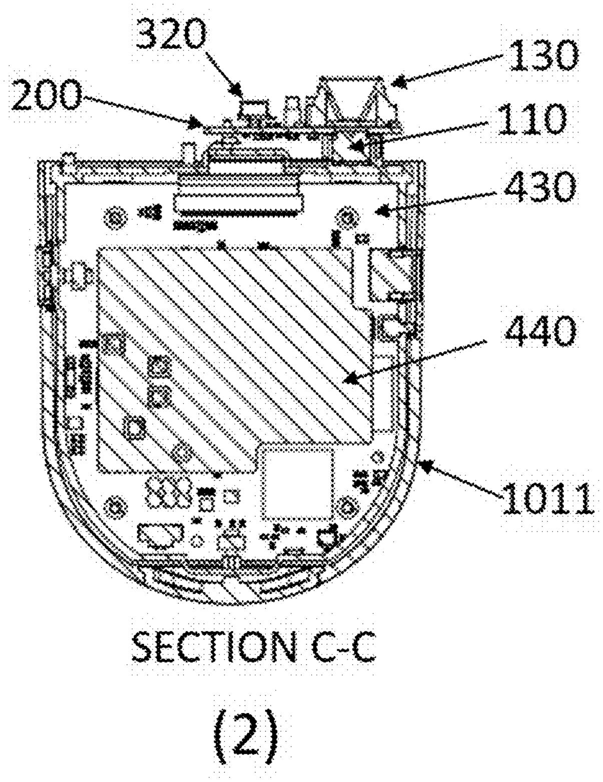

FIG. 3(1) is a top view of a state in which an upper casing 1021 is disassembled from the scalp sensing device 1000 according to one embodiment of the present invention, and FIG. 3(2) is a perspective view of the upper casing 1021.

The scalp sensing device 1000 according to one embodiment of the present invention includes a main body part 1010 and a sensor module 1020 coupled to one side (upper portion) of the main body part. The main body part and the sensor module each have internal parts accommodated by a lower casing 1011 and the upper casing 1021. The structures or cover ranges of the casings may be subject to design changes and are not limited to those illustrated in the drawings.

According to one embodiment of the present invention, the main body part 1010 includes components such as a battery 420, a main printed circuit board (PCB) 430, a main body frame 410 to which the battery and the main PCB are fixed, and a heat sink 440 and the lower casing 1011 configured to accommodate the components. The main body frame 410 has a T-shape and is fixed in the lower casing 1011. The battery 420, the main PCB 430, and the heat sink 440 are fixed to the main body frame 410.

The main body frame 410 includes a main body support plate 411 longitudinally extending vertically and an upper support plate 412 coupled to an upper end of the main body support plate 411. A seating portion 413 for a camera to be seated thereon is formed on an upper surface of the upper support plate 412 (see FIGS. 4 and 5).

Figure 6:
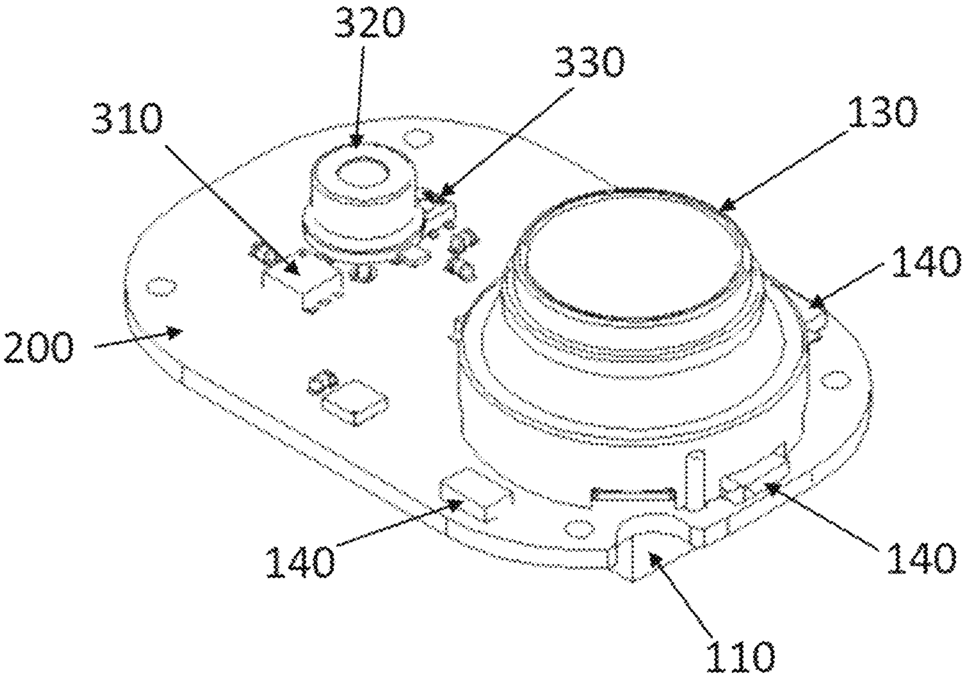
FIG. 6 is a perspective view of a sensor module of the scalp sensing device (1000) according to one embodiment of the present invention.
Figure 8:
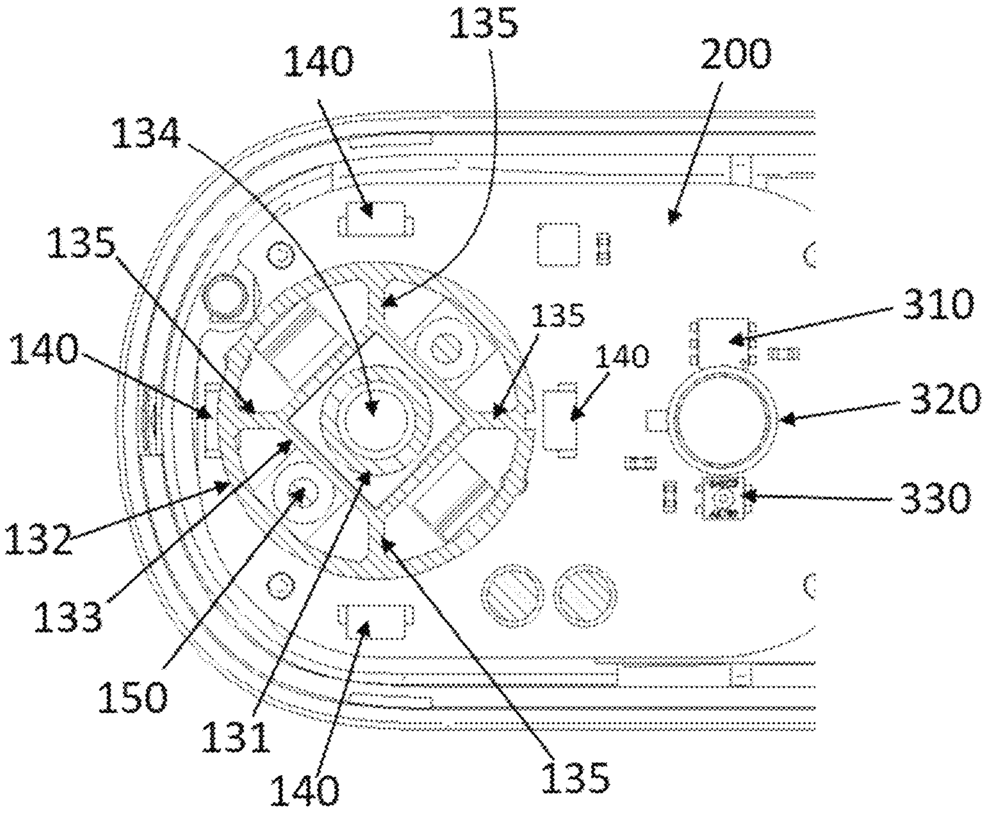
FIG. 8 is a transverse cross-sectional view of the sensor module of the scalp sensing device (1000) according to one embodiment of the present invention.
Figure 9:
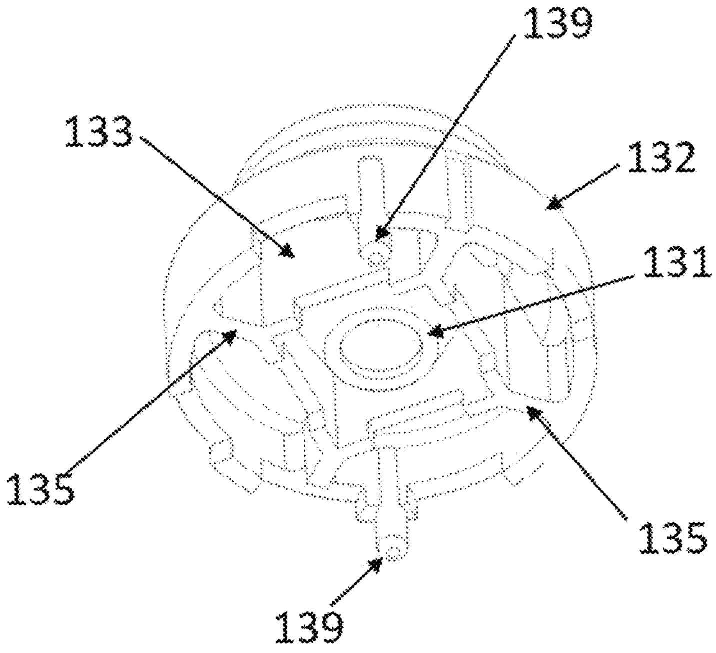
FIG. 9 is a bottom perspective view of a light diffusion member of the scalp sensing device (1000) according to one embodiment of the present invention.

Meanwhile, referring to FIGS. 3, 6, and 8, a sensor module 1100 includes a sensor board 200, a camera module 100, and scalp environment sensors 310, 320, and 330. The sensor board 200 may be a PCB to which the camera module 100 and the scalp environment sensors 310, 320, and 330 are mechanically fixed and which has an internal circuit to which the camera module 100 and the scalp environment sensors 310, 320, and 330 are electrically connected, but the sensor board 200 may also be a physical support part on which the camera module 100 and the scalp environment sensors 310, 320, and 330 are mounted without electrical connections.

The camera module 100 is disposed in one region of the sensor board 200, and the scalp environment sensors 310, 320, and 330 are disposed in another region of the sensor board adjacent to the camera module. The camera module 100 and the scalp environment sensors 310, 320, and 330 according to one embodiment of the present invention are disposed adjacent to each other, and due to such a structure, when a scalp image is captured by the camera module of the scalp sensing device approaching the scalp of a user, the scalp environment sensors may also approach the region of the scalp that is being captured and simultaneously measure one or more pieces of scalp sensing data among scalp temperature data, scalp moisture data, and scalp smell data.

Hereinafter, the structure of the sensor module will be described in detail with reference to FIGS. 5 to 10.

First, the structure of the camera module will be described. The camera module includes a camera part 110 including an image sensor and a lens and positioned under a through-hole of the sensor board, a light diffusion member 130 disposed on an optical axis of the camera part, a blue-cut filter 120 disposed between the camera part and the light diffusion member to block the through-hole and block light of a predetermined wavelength that is incident on the camera part, a UV light source 150, and a white light source 140.

Figure 5:
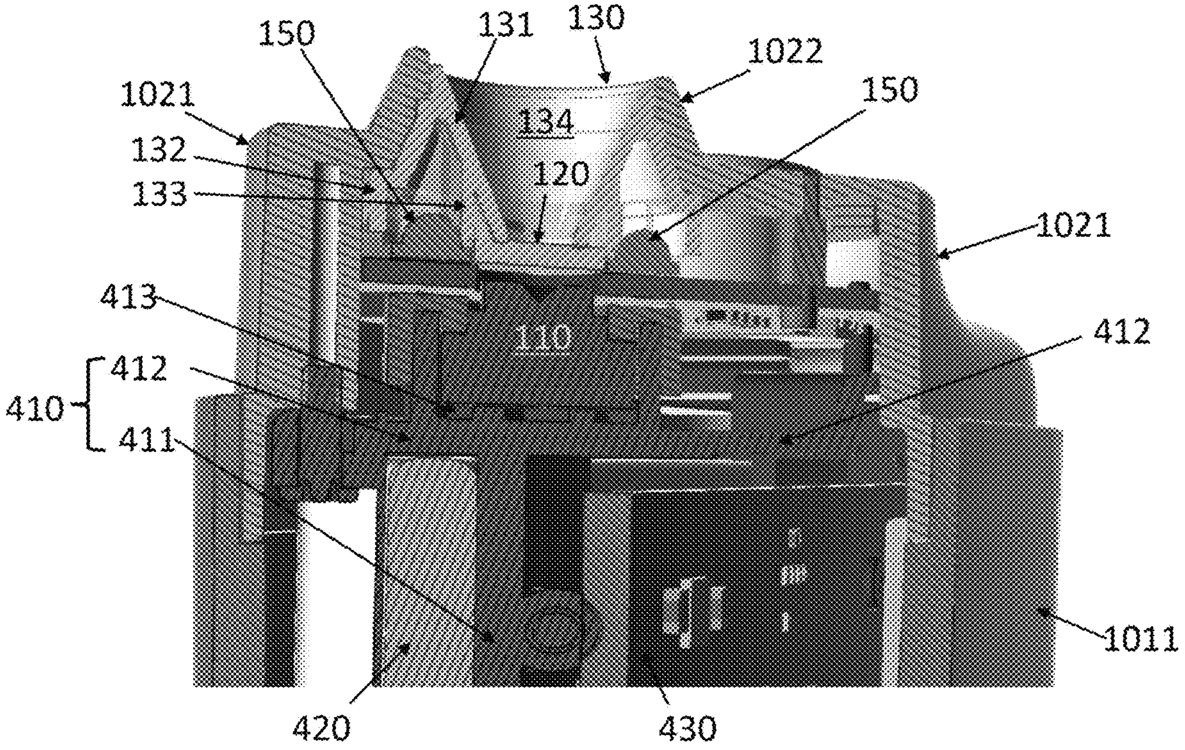
FIG. 5 is a longitudinal cross-sectional view of a portion of the scalp sensing device (1000) according to one embodiment of the present invention.
Figure 7:
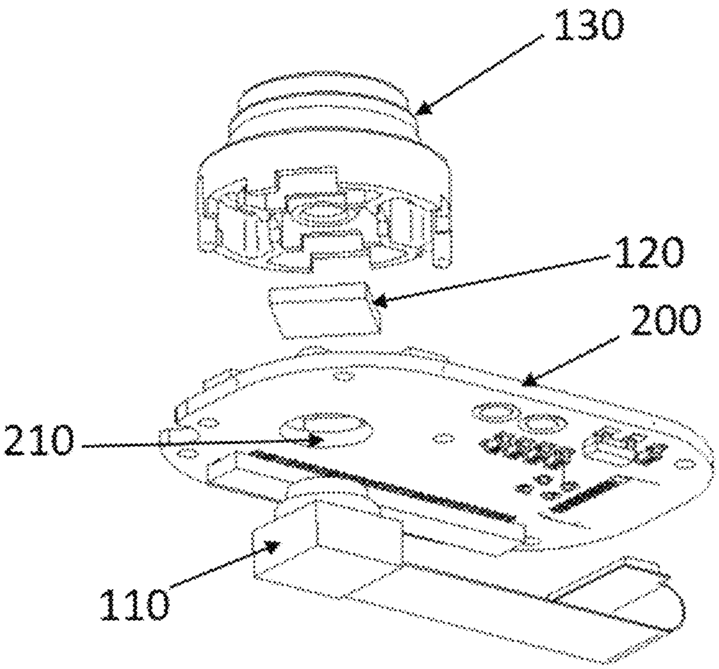
FIG. 7 is an exploded perspective view of the sensor module of the scalp sensing device (1000) according to one embodiment of the present invention.

Referring to FIGS. 5 to 7, the sensor board 200 is disposed at an upper portion of the main body frame 410, and a through-hole 210 is formed in one region of the sensor board 200. The camera part 110 is disposed under the through-hole 210. The camera part 110 consists of an image sensor and a lens coupled to an upper portion of the image sensor and is fixed by being seated on the seating portion 413 formed at an upper portion of the main body frame 410.

The blue-cut filter is fixed and coupled to an upper end of the through-hole 210. The blue-cut filter 120 is coupled to the sensor board 200 around the through-hole 210 by, for example, heat fusion and blocks the through-hole 210 from above the through-hole 210 to filter light of a specific wavelength (for example, in a range of 360 nm to 440 nm) that is introduced into the camera through the through-hole.

The light diffusion member 130 is disposed at an upper portion of the blue-cut filter. The light diffusion member 130 is fixed and coupled to an upper surface of the sensor board 200 by, for example, heat fusion. That is, the light diffusion member 130 is fixed and coupled to an upper portion of the through-hole of the sensor board 200 with the blue-cut filter 120 disposed therebetween.

The light diffusion member 130 is a one-body type diffusion lens having a conical shape or a cylindrical shape with a cut upper end and is configured to effectively guide light of the white light source and the UV light source, which are fixed and coupled to the sensor board 200, to a measurement target scalp region at an upper end and allow reflected light to be optimally incident on the camera part. The light diffusion member 130 may be made of transparent plastic, for example, polymethyl methacrylate (PMMA), polycarbonate (PC), or polyurethane (PU). The light diffusion member 130 may be formed as one body using a mold but is not limited thereto.

The light diffusion member 130 according to one embodiment of the present invention has a double cylinder structure in which an inner cylinder 131 having a hollow portion 134 formed therein and an outer cylinder 132, which has an upper end connected to the inner cylinder 131, are coupled along a central axis of the hollow portion 134. The inner cylinder 131 and the outer cylinder 132 are coaxial, are connected at an upper portion to share the same inner and outer circumferential surfaces, and are spaced apart from each other at a lower portion so that a lower space is formed between the inner and outer cylinders. Here, "cylinder" is used as a concept encompassing a truncated cone, a quadrangular pyramid, and a polygonal pyramid. At the upper portion of the light diffusion member 130, the outer cylinder and the inner cylinder are integrated with each other and have the same radius. On the other hand, at the lower portion of the light diffusion member 130, a lower radius of the inner cylinder is smaller than a lower radius of the outer cylinder, and the inner and outer cylinders 131 and 132 are spaced apart from each other such that a space is formed therebetween. The space is for placing the UV light source, or a UV-A LED 150, in a state in which the sensor module is assembled.

According to one embodiment of the present invention illustrated in FIG. 5 and FIGS. 8 to 10, the inner cylinder of the light diffusion member 130 has a conical shape with a cut lower portion, and the outer cylinder has a conical shape with a cut upper end. The outer cylinder 132 of the light diffusion member 130 may have a conical shape in which a lower diameter is larger than an upper diameter, and the diameter gradually decreases upward with a step difference, but the shape of the outer cylinder 132 is not limited thereto and may also be a simple cylindrical shape or a polygonal pyramidal shape. The inner cylinder 131 may have a truncated conical shape in which an upper diameter is larger than a lower diameter but may also have a polygonal pyramidal shape in which an upper cross-sectional area is larger than a lower cross-sectional area. In a process of assembling the sensor module, a lower end of the inner cylinder 131 presses an upper end surface of the blue-cut filter 120 fixed to the sensor board 200, thus facilitating fixing of the position of the blue-cut filter to the through-hole 210 and reliably closing the through-hole 210 to prevent the light of the predetermined wavelength from entering the camera part.

An intermediate portion 133 having the shape of a quadrangular column may be additionally formed on the circumference of the inner cylinder of the light diffusion member 130 and may be disposed between the inner cylinder and the outer cylinder. The intermediate portion 133 may be a quadrangular cylinder that is branched downward from an upper coupling portion of the inner cylinder and the outer cylinder and extends vertically. An inner circumferential surface of a lower end of the intermediate portion 133 may be formed to correspond to the blue-cut filter to circumscribe a side edge of the blue-cut filter. Parts of the intermediate portion 133 excluding four corners thereof may be cut out. The four corners of the intermediate portion are tightly placed around four corners of the blue-cut filter in an assembled state and provide support for fixing the position of the blue-cut filter in the assembling process.

Four connecting portions 135 may be formed to radially extend from the four corners of the intermediate portion 133 of the light diffusion member 130 and be connected to the outer cylinder 132. Each connecting portion 135 is connected to the outer cylinder by radially extending horizontally about the central axis (optical axis) from one of the corners of the intermediate portion 133.

Referring to FIGS. 5 and 8, a UV-A LED is disposed in each space surrounded by two connecting portions 135 adjacent to each other and the sensor board at a lower portion, between the outer cylinder 132 and the intermediate portion 133. That is, two UV-A LEDs 150 are coupled onto the sensor board 200 between the outer cylinder and the intermediate portion while disposed to be symmetrical about the optical axis and are disposed between the two connecting portions 135. Meanwhile, referring to FIGS. 6 and 8, four white LEDs 140 are each disposed to face an outer side of one of the four connecting portions 135 on the sensor board.

The arrangement and action of the UV-A LEDs 150 will be described in detail with reference to FIGS. 5 and 11.

Figure 11:
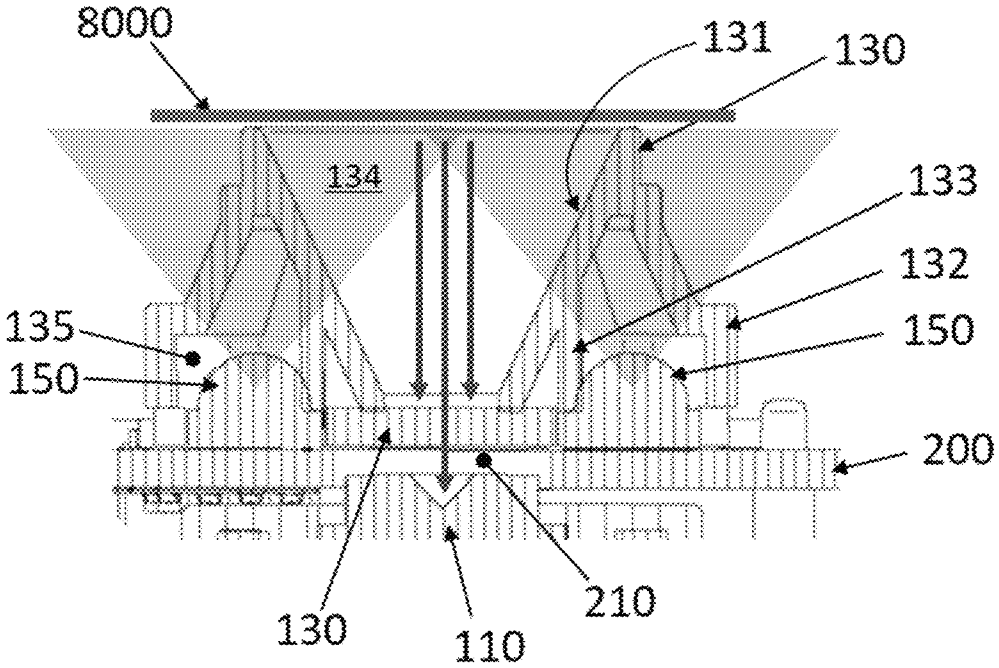
FIG. 11 is another longitudinal cross-sectional view of the camera module of the scalp sensing device according to one embodiment of the present invention and shows paths of light emitted from an ultraviolet (UV) light source and light incident from a measurement target region.
Figure 12:
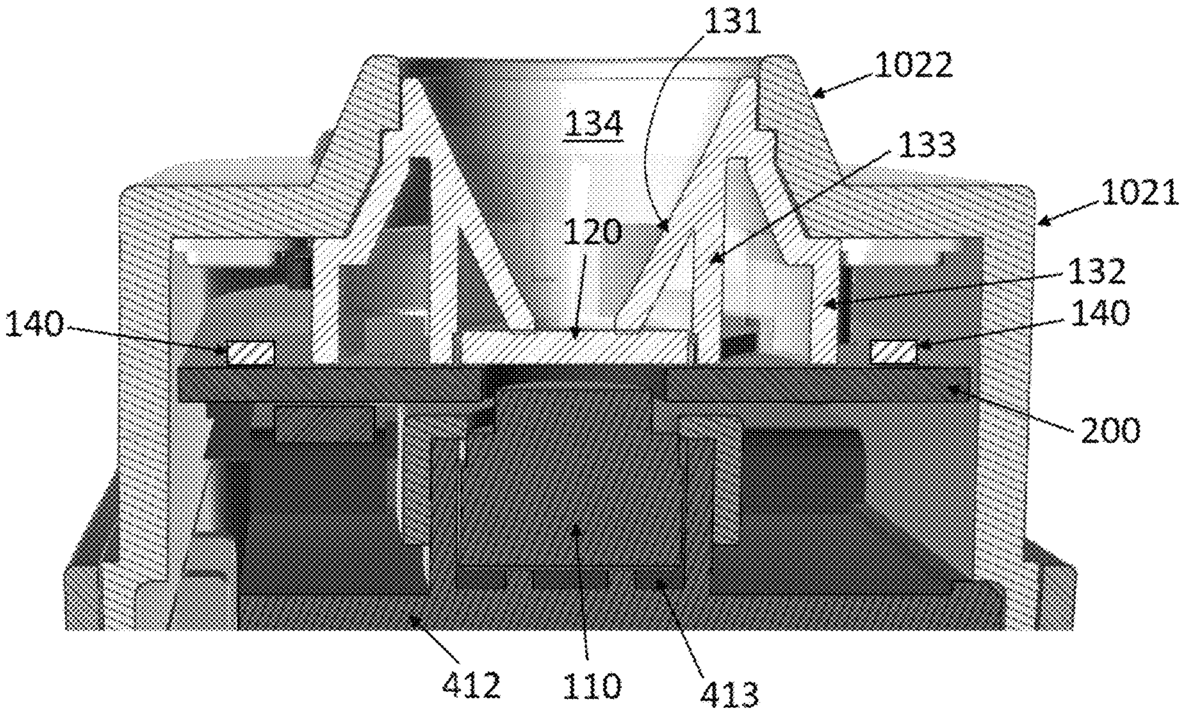
FIG. 12 is a cross-sectional view showing a state in which the upper casing is coupled to the sensor module of FIG. 10.

Referring to FIG. 11, UV-A light (whose central wavelength is 365 nm) is diffused and directed upward from the UV-A LEDs 150 disposed on the sensor board 200 between the outer cylinder 132 and the inner cylinder 131 or the intermediate portion 133. In FIG. 11, diffusion directions and distributions of light emitted from the UV-A LEDs 150 are shaded in. However, FIG. 11 shows a state in which the upper casing is not applied, and in the sensing device 1000 in an assembled state, the upper casing made of a non-light-transmissible material is fitted to an outer side of an upper portion of the outer cylinder 132 (see FIG. 5). Therefore, some of the UV light directed to the outer cylinder 132 is internally reflected and illuminated to a surface 8000 of the scalp (skin) to be measured. Due to a UV fluorescence excitation phenomenon, sebum, dead follicles, and inflammation emit white-orange visible light (sebum), purple-black visible light (dead follicles), and orange-red visible light (inflammation), respectively. The emitted and scattered light are irradiated in the directions indicated by arrows in FIG. 11 and pass through the hollow portion 134, the blue-cut filter 120, and the through-hole 210 and constitute an image captured by the camera part.

Light incident on the camera part is supposed to pass through the through-hole, but since the through-hole is blocked by the blue-cut filter, light in the blue wavelength band (360 nm to 440 nm) that overlaps with wavelengths of light of the UV-A LEDs may be effectively filtered.

Figure 10:
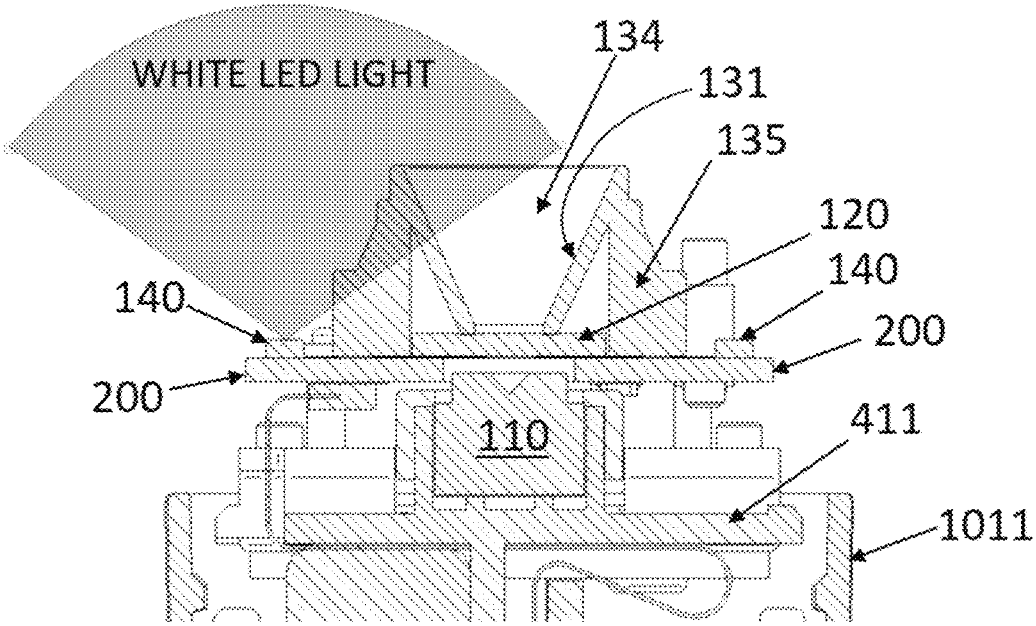
FIG. 10 is a longitudinal cross-sectional view of a camera module of the scalp sensing device (1000) according to one embodiment of the present invention.

Meanwhile, as illustrated in FIGS. 8 and 10, the four white LEDs are fixed onto the sensor board 200 at an outer side of the light diffusion member 130. Referring to FIG. 8, each of the four white LEDs is disposed to be adjacent to one of the four connecting portions 135 that radially extend from the four corners of the intermediate portion 133 and are connected to the outer cylinder 132. Referring to FIG. 8, each of the four white LEDs is disposed to face one of the four connecting portions 135, but two, three, or more white LEDs may be disposed to face the corresponding connecting portions 135.

Referring to FIG. 10, white light is diffused upward, and some of the white light is directly guided by the light diffusion member. Some of the white light reflected and scattered from inside the camera part cap of the upper casing is directed to the outside via the hollow portion 134 through the light diffusion member. In particular, some of the light emitted from the white LEDs 140 may be effectively delivered to an upper portion of the hollow portion at an inner side along a structure in which the outer cylinder, the connecting portions, and the intermediate portion are integrally formed.

In FIG. 10, diffusion directions and distributions of light emitted from the white LEDs 140 are shaded in. However, FIG. 10 shows a state in which the upper casing is not applied, and in the sensing device 1000 in an assembled state, the upper casing made of a non-light-transmissible material is disposed at outer and upper sides of the white LEDs 140. As in FIG. 12, an inner surface of the upper casing may reflect some of the light from the white LEDs 140 and guide some of the light to the light diffusion member.

In this way, an optical system of the present invention has been designed so that the UV light sources and the white light sources are disposed adjacent to the camera part at a lower portion, and light from the light sources is directed to a measurement target site, and then reflected/scattered or excited, and incident on the camera part positioned in the opposite direction again. Due to such a structure, light from the light sources may be used with maximum efficiency. However, in the structure, the light sources, the camera part, and the like are disposed in a very narrow region, but paths of reflected light before and after the light reaches a measurement target region should be made different, and thus it is difficult to design space arrangement and optical paths. The inventor of the present invention has addressed such problems using the light diffusion member having the double cylinder structure having the hollow portion.

Meanwhile, by a controller of the main PCB or the sensor board, the white LEDs 140 and the UV-A LEDs 150 are controlled to sequentially emit light instead of simultaneously emitting light. The white LEDs 140 may emit light first so that the camera part 110 captures an image of a measurement target region, and then the UV-A LEDs 150 may emit light at several ms intervals to illuminate the measurement target region with UV light so that the camera part 110 captures a UV excitation image. The continuous light emitting and image capturing processes are performed at several us intervals or several s intervals such that matching images for the same region are almost simultaneously obtained. Further, since the images of the same region are almost simultaneously captured by the same optical system, it is easy to match a typical scalp image and a UV-induced fluorescence image.

Figure 13:
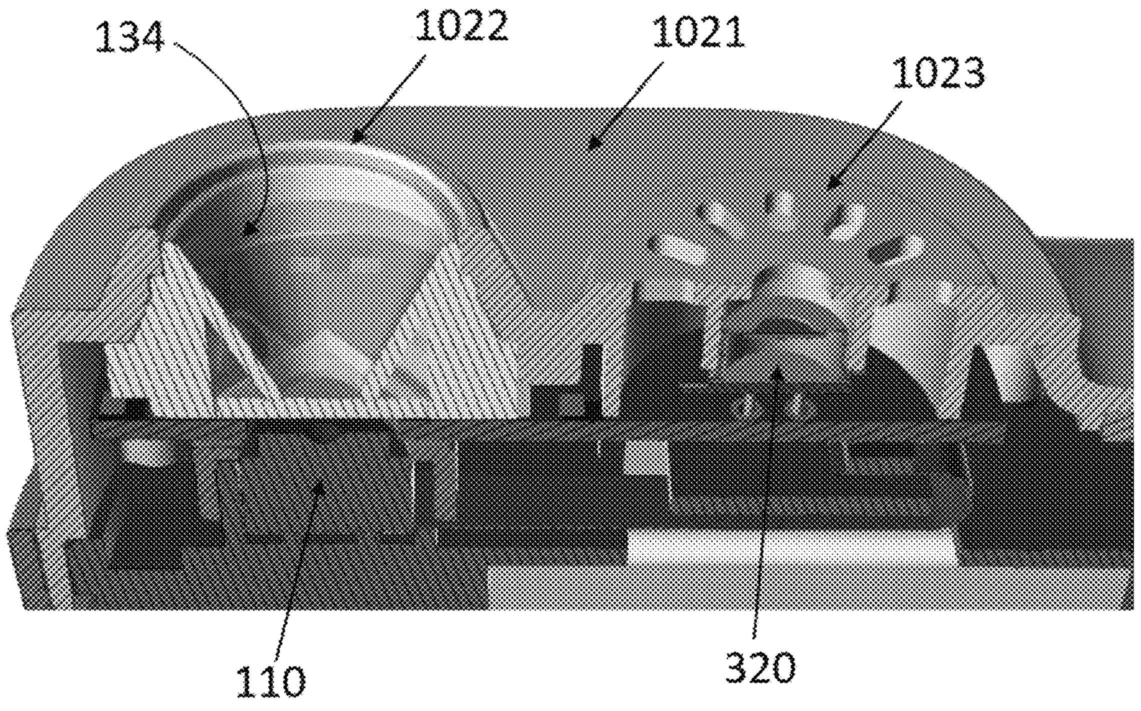
FIG. 13 is a partial cut-out view of the scalp sensing device according to one embodiment of the present invention.

Meanwhile, the upper casing covers an upper portion of the sensor module, and a camera part cap 1022 and an environment sensor cap 1023 are each formed in a protruding cylindrical shape in regions of the upper casing that correspond to the camera module and the scalp environment sensors of the sensor module (see FIGS. 3 and 13). The camera part cap 1022 protrudes in a cylindrical shape with an open upper end on one region of an upper surface of the upper casing, and the environment sensor cap 1023 is formed in a protruding cylindrical shape having a plurality of through-holes formed in an upper surface thereof and is disposed adjacent to the camera part cap. Upper portions of the camera module and the scalp environment sensors are each covered by the camera part cap 1022 and the environment sensor cap 1023 formed on the corresponding regions of the upper casing.

A transparent cover is coupled to an upper end of the camera part cap so that light from the camera part and reflected/scattered light from the scalp pass therethrough while foreign matter is prevented from entering the camera module from the outside. An upper portion of the camera part cap is fitted to the upper portion of the light diffusion member. The camera part cap protrudes upward slightly more than the environment sensor cap and comes in close contact with the scalp or skin, and thus introduction of disturbance light may be minimized during imaging. When the camera part cap comes in close contact with the scalp or skin for measurement, the environment sensor cap 1023 adjacent to the camera part cap and whose height is slightly lower than the camera part cap is slightly spaced apart from the measurement target surface, and thus foreign matter may be prevented from entering the environment sensor cap 1023 while measurement of temperature, moisture, and smell is facilitated.

Scalp environment sensors 300 may include a temperature sensor 320, a moisture sensor 310, and/or a volatile organic compound (VOC) sensor 330 configured to detect volatile organic matter and measure a smell, and scalp temperature data, scalp moisture data, and/or scalp smell data may be obtained through the sensors, respectively. The data may be the basis for calculating alopecia diagnosis aid information according to one embodiment of the present application.

Figure 14:
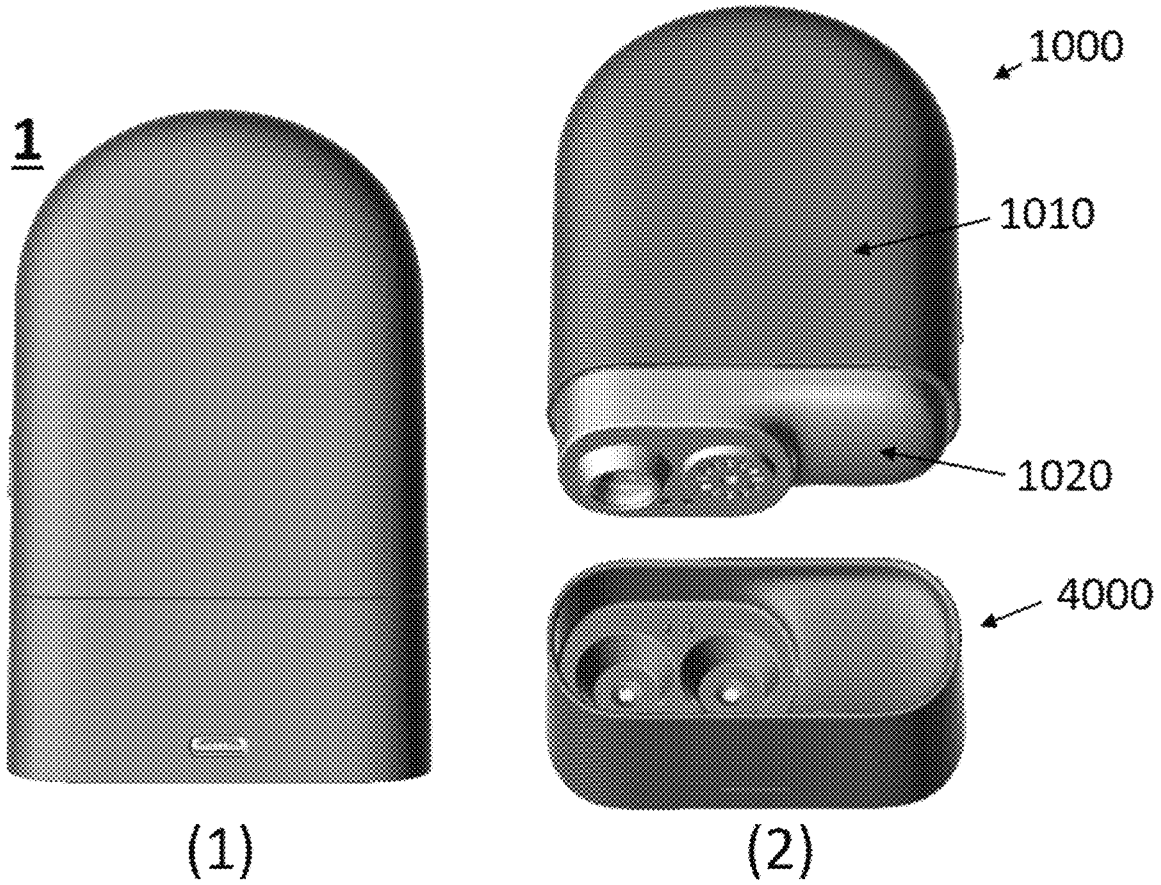
FIG. 14 shows perspective views of (1) a state in which the scalp sensing device according to one embodiment of the present invention is mounted on a cradle and (2) a state in which the scalp sensing device is separated from the cradle.

FIG. 14(1) is a perspective view showing a state in which the scalp sensing device 1000 according to one embodiment of the present invention is seated on a cradle 4000, and FIG. 14(2) is a perspective view showing a state in which the scalp sensing device 1000 is separated from the cradle 4000. The scalp sensing device 1000 may have the cradle 4000 that allows the scalp sensing device 1000 to be mounted thereon and includes a charging terminal and a UV-C LED for sterilization.

Figure 15:
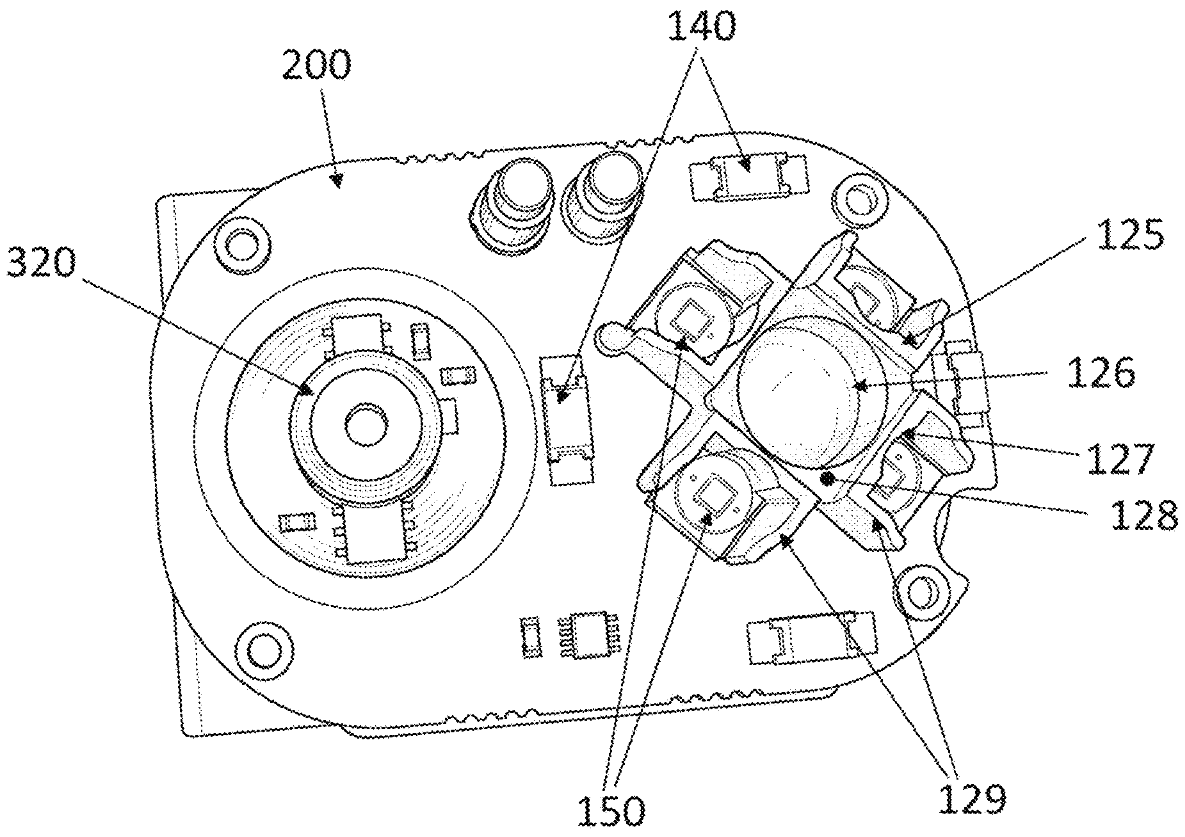
FIG. 15 is a top view of a portion of a sensor module of a scalp sensing device (1000) according to another embodiment of the present invention.

A sensor module of the scalp sensing device 1000 according to another embodiment of the present invention will be described with reference to FIG. 15. In the embodiment of FIG. 15, descriptions of parts identical to the above-described embodiment will be omitted, and only differences will be described.

The sensor module of the scalp sensing device 1000 according to another embodiment of the present invention further includes a separation plate 125 disposed under the light diffusion member 130. The separation plate 125 is made of a non-light-transmissible material and has a through-portion 126 formed at the center and a blocking wall 127 formed to protrude upward from a circumference of the through-portion at the center.

The blue-cut filter 120 is seated on a seating portion 128 formed at the blocking wall and is positioned at an upper end of the through-portion 126, and a central axis of the through-portion at the center is coaxial with the optical axis. The UV light source 150 is disposed at an outer side of the blocking wall 127. The blocking wall 127 is formed to protrude in a quadrangular shape from the circumference of the through-portion at the center, an extension wall 129 is formed to radially extend outward from the blocking wall 127, and the UV light source 150 is disposed between the blocking wall 127 and the extension wall 129.

The white light source is positioned more outward from the optical axis than the UV light source and is alternately disposed with the UV light source. The light diffusion member is disposed on the separation plate to press the blue-cut filter 120. Here, the light diffusion member may have a form similar to the form thereof in the above-described embodiment of FIGS. 2 to 14.

Figure 16:
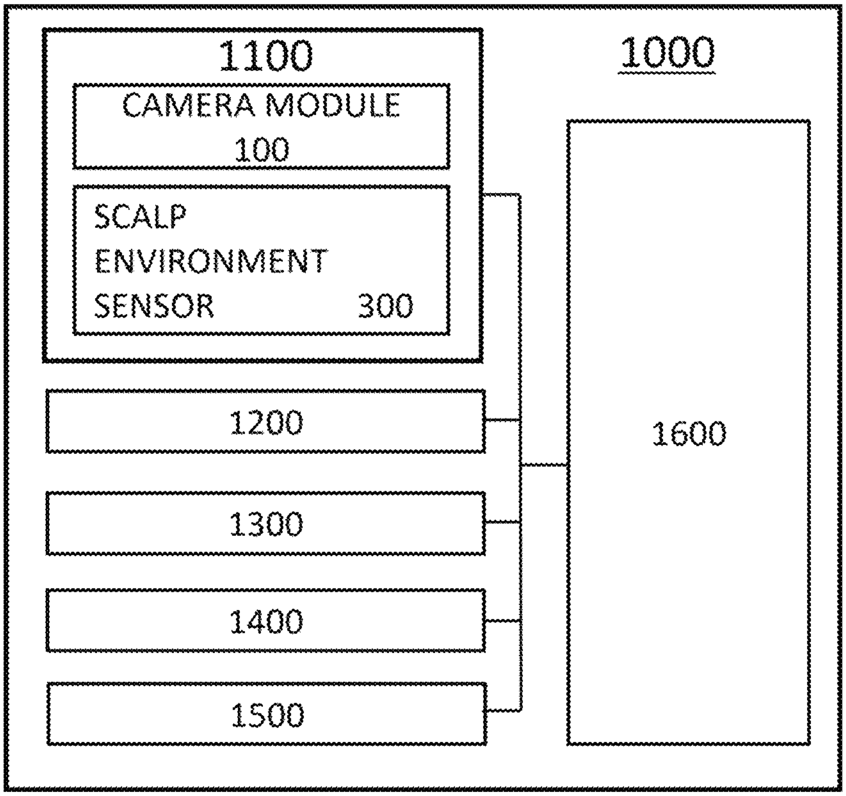
FIG. 16 is a schematic structural diagram of the scalp sensing device according to an embodiment of the present invention.

The scalp sensing device 1000 according to one embodiment of the present application will be functionally described in terms of control with reference to FIG. 16 which is a schematic block diagram of the scalp sensing device 1000 according to embodiments of the present invention.

The scalp sensing device 1000 according to one embodiment of the present application may include the sensor module 1100, a communication module 1200, a memory 1300, an input button 1400, an output display 1500, and a controller 1600.

The sensor module 1100 may include the camera module 100 configured to capture a scalp image. The sensor module 1100 may further include the scalp environment sensors 300 configured to obtain scalp temperature data, scalp moisture data, and scalp smell data. For example, the scalp sensing device 1000 may transmit the obtained scalp image, target image, or scalp sensing data to the electronic device 2000 or the server 3000 through the communication module 1200.

The camera module 100 may be implemented to continuously capture a scalp image when a shooting mode of the scalp sensing device 1000 is activated. Alternatively, the camera module 100 may be implemented to obtain a scalp image based on a user input made through the input button 1400 for requesting capturing of a scalp image.

The communication module 1200 may perform communication with any external device including the electronic device 2000 and the server 3000.

The communication module 1200 may mainly perform wired or wireless communication, and the memory 1300 may store various information. Various data may be temporarily or semi-permanently stored in the memory 1300. Examples of the memory 1300 may include a hard disk drive (HDD), a solid state drive (SSD), a flash memory, a read-only memory (ROM), a random access memory (RAM), and the like.

The memory 1300 may be provided in a form that is embedded in the scalp sensing device 1000 or a form that is attachable to and detachable from the scalp sensing device 1000. Various data necessary for the operation of the scalp sensing device 1000, including an operating system (OS) for driving the scalp sensing device 1000 or a program for operating each component of the scalp sensing device 1000, may be stored in the memory 1300. For example, various data relating to a scalp image and information relating to a target image may be stored in the memory 1300.

Meanwhile, the scalp sensing device 1000 may obtain a user input and output information corresponding to the user input using the input button 1400 and the output display 1500. For example, the scalp sensing device 1000 may, using the input button 1400, obtain a user input requesting obtaining of data such as a scalp image and may output information corresponding thereto through the output display 1500.

As one example, a user may request activation of the sensor module 1100 of the scalp sensing device 1000 through the input button 1400. As another example, a user may request to obtain of a scalp image, scalp temperature data, scalp moisture data, and/or scalp smell data through the input button 1400.

The output display 1500 may be provided to output scalp-related information obtained by the scalp sensing device 1000. For example, the output display 1500 may be provided to output a scalp image obtained by the scalp sensing device 1000 to the user.

The controller 1600 may control the overall operation of the scalp sensing device 1000. For example, the controller 1600 may load a program for the operation of the scalp sensing device 1000 from the memory 1300 and run the program.

The controller 1600 may be implemented as an application processor (AP), a central processing unit (CPU), or a device similar thereto according to hardware such as a processor in the main PCB 430, software, or a combination thereof. In terms of hardware, the controller 1600 may be provided in the form of an electronic circuit that processes electrical signals and performs control functions, and in terms of software, the controller 1600 may be provided in the form of programs or codes that drive the hardware circuit.

The electronic device 2000 may be implemented to receive a scalp image from the scalp sensing device 1000 and select a target image. The electronic device 2000 may transmit the selected target image to the server 3000 through an arbitrary network.

According to one aspect of the present invention, there is provided a scalp sensing device that is easy to carry and can obtain various scalp measurement data by (almost) simultaneous measurement using a single camera part.

The present invention also provides a small-sized sensing device with ease of assembly, convenience in use, and an improved data quality, and a scalp analysis system including the same.

The features, structures, effects, and the like described in the above embodiments are included in at least one embodiment of the present invention and are not necessarily limited to only one embodiment. Further, the features, structures, effects, and the like described in each embodiment may be combined or modified for other embodiments by those of ordinary skill in the art to which the embodiments pertain. Therefore, the content relating to such combinations and modifications should be construed as belonging to the scope of the present invention.

Also, the present invention has been described above using the embodiments thereof, but the description is merely illustrative, and the present invention is not limited thereby. Those of ordinary skill in the art to which the present invention pertains should understand that various modifications and applications not described above are possible within the scope not departing from the essential characteristics of the present embodiments. That is, each component described in detail in the embodiments may be modified. Also, differences relating to such modifications and applications should be construed as belonging to the scope of the present invention defined by the appended claims.

What is claimed is:

1. A scalp sensing device that is portable comprising a camera module, the camera module comprising:

a camera part including an image sensor and a lens, a light diffusion member disposed on an optical axis of the camera part, a blue-cut filter disposed between the camera part and the light diffusion member to block light of a predetermined wavelength that is incident on the camera part, a UV light source, and at least one white light source, wherein the light diffusion member, is configured to diffuse and guide light emitted from each of the at least one white light source and the UV light source to direct the light onto a measurement target region, is formed as a one body of a transparent plastic material and has a double cylinder structure comprising an inner cylinder with a hollow portion along a central axis thereof and an outer cylinder, which is joined to the inner cylinder at an upper end and extends downward therefrom;

wherein the camera part is configured to capture an image of the measurement target region illuminated by the light; and wherein the UV light source is disposed between the inner cylinder and the outer cylinder.

2. The scalp sensing device of claim 1, wherein:

the predetermined wavelength is in a range of 360 nm to 440 nm;

the UV light source is a UV-light emitting diode (LED) that is disposed under the light diffusion member;

the at least one white light source is an LED that is disposed adjacent to an outer side of the light diffusion member;

the at least one white light source and the UV light source are configured to sequentially emit light; and the camera part is configured to sequentially obtain an image of the measurement target region illuminated by white light and a porphyrin excitation image of the measurement target region illuminated by UV light.

3. The scalp sensing device of claim 1, further comprising a support plate having a through-hole formed therein, wherein the blue-cut filter is disposed at an upper end of the through-hole and blocks the through-hole, the camera part is disposed at a bottom portion of the through-hole;

the camera part detects light incident through the blue-cut filter and the through-hole, and the at least one white light source includes a plurality of white light sources fixed to the support plate and disposed to be symmetrical about the optical axis at an outer side of the light diffusion member.

4. The scalp sensing device of claim 1, wherein:

the central axis of the hollow portion is coaxial with the optical axis;

the inner cylinder and the outer cylinder are coaxial, are connected at an upper portion, and are spaced apart from each other at a lower portion so that a lower space is formed between the inner and outer cylinders;

an intermediate portion is formed around the inner cylinder and disposed between the inner cylinder and the outer cylinder; and the intermediate portion is branched downward from an outer circumferential portion of the inner cylinder and extends vertically, and an inner circumferential surface of a lower end of the intermediate portion is configured in a shape corresponding to the blue-cut filter to circumscribe a side edge of the blue-cut filter.

5. The scalp sensing device of claim 1, wherein:

one or more connecting portions are formed to radially extend from the inner cylinder of the light diffusion member about the optical axis and be connected to the outer cylinder; and the at least one white light source is disposed adjacent to outer sides of the one or more connecting portions so that each of the at least one white light source faces one of the connecting portions.

6. A portable scalp sensing device comprising:

a camera module comprising a camera part including an image sensor and a lens, a light diffusion member disposed on an optical axis of the camera part, a blue-cut filter disposed between the camera part and the light diffusion member to block light of a predetermined wavelength that is incident on the camera part, a UV light source, and at least one white light source;

a scalp environment sensor; and an upper casing configured to cover the camera module and the scalp environment sensor, wherein the light diffusion member is configured to diffuse and guide light emitted from each of the at least one white light source and the UV light source to direct the light onto a measurement target region, wherein the camera part is configured to capture an image of the measurement target region illuminated by the light, wherein the scalp environment sensor includes one or more of a temperature sensor, a moisture sensor, and a volatile organic compound (VOC) sensor fixed onto the support plate, the camera module is disposed adjacent to the scalp environment sensor, the upper casing includes a camera part cap configured to tightly cover an upper portion of the light diffusion member disposed on an upper end of the camera part and an environment sensor cap configured to cover the scalp environment sensor, and a plurality of through-holes are formed in the environment sensor cap.

7. The scalp sensing device of claim 6, wherein the camera part cap has a cylindrical shape and is able to come in close contact with the scalp while a scalp image is being captured.

8. A portable scalp sensing device comprising:

a camera module comprising a camera part including an image sensor and a lens, a light diffusion member disposed on an optical axis of the camera part, a blue-cut filter disposed between the camera part and the light diffusion member to block light of a predetermined wavelength that is incident on the camera part, a UV light source, and at least one white light source; and a cradle for mounting the scalp sensing device, wherein the light diffusion member is configured to diffuse and guide light emitted from each of the at least one white light source and the UV light source to direct the light onto a measurement target region, wherein the camera part is configured to capture an image of the measurement target region illuminated by the light, and wherein the cradle includes an electrical contact part for charging and a UV sterilizer.

9. A portable scalp sensing device comprising:

a camera module comprising a camera part including an image sensor and a lens, a light diffusion member disposed on an optical axis of the camera part, a blue-cut filter disposed between the camera part and the light diffusion member to block light of a predetermined wavelength that is incident on the camera part, a UV light source, and at least one white light source; and a separation plate disposed under the light diffusion member, wherein the separation plate is made of a non-light-transmissible material and has a through-portion formed at a center and a blocking wall formed to protrude upward from a circumference of the through-portion, the blue-cut filter is seated on a seating portion formed at the blocking wall and is positioned at an upper end of the through-portion, a central axis of the through-portion at the center is coaxial with the optical axis, the UV light source is disposed at an outer side of the blocking wall, the at least one white light source is positioned more outward from the optical axis than the UV light source, and the light diffusion member is disposed on the separation plate.

10. A sensing device for sensing skin or scalp, the sensing device comprising:

a main body part including a battery, a main printed circuit board (PCB), and a main body frame to which the battery and the main PCB are fixed; and a sensor module coupled to the main body part and including a camera module mounted on a sensor board, wherein the camera module includes a camera part including an image sensor and a lens and positioned under a through-hole of the sensor board, a light diffusion member disposed on an optical axis of the camera part, a blue-cut filter disposed between the camera part and the light diffusion member to block the through-hole and block light of a predetermined wavelength that is incident to the camera part, a UV light source, and a white light source, the light diffusion member diffuses and guides light emitted from each of the white light source and the UV light source to illuminate a measurement target region with the light, the camera part obtains images of the measurement target region by detecting light passing through the through-hole through the blue-cut filter, the light diffusion member is formed as a one body made of a transparent plastic material and has a double cylinder structure comprising an inner cylinder with a hollow portion along a central axis thereof and an outer cylinder, which is joined to the inner cylinder at an upper end and extends downward therefrom, and the UV light source is disposed between the inner cylinder and the outer cylinder.

11. The sensing device of claim 10, wherein:

the main PCB includes a memory, a processor, and a communication module;

the sensor module includes an environment sensor disposed adjacent to the camera module on the sensor board; and the environment sensor includes one or more of a temperature sensor, a moisture sensor, and a volatile organic compound (VOC) sensor fixed onto the sensor board.

12. The sensing device of claim 10, wherein:

the sensor module is covered by an upper casing;

the upper casing includes a camera part cap formed to protrude to tightly cover an upper portion of the light diffusion member; and the camera part cap is able to come in close contact with the scalp or skin while an image thereof is being captured.

13. A scalp analysis system comprising:

the scalp sensing device of claim 1;

an electronic device; and a server, wherein the scalp sensing device obtains scalp sensing data of a human or an animal and sends the scalp sensing data to the electronic device or the server through a communication network, and the scalp sensing data is scalp image data, scalp temperature data, scalp moisture data, or scalp smell data.

* * * * *